United States Patent
Jikuhara et al.

(10) Patent No.: US 12,391,278 B2
(45) Date of Patent: Aug. 19, 2025

(54) INFORMATION PROCESSING APPARATUS, NON-TRANSITORY COMPUTER READABLE MEDIUM, AND INFORMATION PROCESSING METHOD

(71) Applicant: TOYOTA JIDOSHA KABUSHIKI KAISHA, Toyota (JP)

(72) Inventors: Yoshikazu Jikuhara, Miyoshi (JP); Shin Sakurada, Toyota (JP); Tomokazu Maya, Nagoya (JP); Hiroyuki Bandai, Toyota (JP); Hiromitsu Fujii, Kariya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 203 days.

(21) Appl. No.: 18/455,042

(22) Filed: Aug. 24, 2023

(65) Prior Publication Data
US 2024/0075952 A1    Mar. 7, 2024

(30) Foreign Application Priority Data
Aug. 25, 2022  (JP) .................. 2022-134434

(51) Int. Cl.
*B60W 60/00*   (2020.01)
*A61B 5/16*   (2006.01)
*G06Q 10/02*   (2012.01)

(52) U.S. Cl.
CPC ......... *B60W 60/0013* (2020.02); *A61B 5/165* (2013.01); *G06Q 10/02* (2013.01)

(58) Field of Classification Search
CPC . B60W 60/0013; B60N 2/885; B60N 2/0273; A61H 15/0078; G06N 3/08; B25J 9/1676; B60P 3/32; A61B 5/0004; G06V 40/174
See application file for complete search history.

(56) References Cited

U.S. PATENT DOCUMENTS

| | | | |
|---|---|---|---|
| 11,436,935 B2 * | 9/2022 | Welles et al. | G06V 40/174 |
| 2014/0265242 A1 * | 9/2014 | Hernandez | B60P 3/32 280/423.1 |
| 2017/0100838 A1 * | 4/2017 | Lewis | B25J 9/1676 |
| 2020/0086778 A1 * | 3/2020 | Jeon | G06N 3/08 |
| 2021/0155136 A1 * | 5/2021 | Kim | B60N 2/0273 |
| 2022/0040034 A1 * | 2/2022 | Son | A61H 15/0078 |
| 2022/0227270 A1 * | 7/2022 | Ishihara | B60N 2/885 |

FOREIGN PATENT DOCUMENTS

| | | | | |
|---|---|---|---|---|
| CN | 106539574 A | * | 3/2017 | A61B 5/0004 |
| JP | H05286355 A | | 11/1993 | |

* cited by examiner

*Primary Examiner* — Yuri Kan
(74) *Attorney, Agent, or Firm* — Dickinson Wright, PLLC (57) ABSTRACT

An information processing apparatus configured to manage a vehicle with a relaxation facility, the information processing apparatus includes a controller configured to acquire stress information regarding a worker working at a workplace, and command the vehicle to move to the workplace based on the acquired stress information.

13 Claims, 8 Drawing Sheets

FIG. 7

INFORMATION PROCESSING APPARATUS, NON-TRANSITORY COMPUTER READABLE MEDIUM, AND INFORMATION PROCESSING METHOD

CROSS-REFERENCE TO RELATED APPLICATION

This application claims priority to Japanese Patent Application No. 2022-134434 filed on Aug. 25, 2022, the entire contents of which are incorporated herein by reference.

TECHNICAL FIELD

The present disclosure relates to an information processing apparatus, a program, and an information processing method.

BACKGROUND

Various technology for reducing user stress has been studied.

For example, Patent Literature (PTL) 1 discloses technology that, by the action of fragrance, allows for relaxed and comfortable use of passenger transport vehicles, thus significantly reducing stress and other problems caused by the use of transportation.

CITATION LIST

Patent Literature

PTL 1: JP H5-286355 A

SUMMARY

Providing relaxing facilities for users (hereinafter referred to as "workers") who work at factories, plants, commercial facilities, offices, and the like (hereinafter referred to as "workplaces") in close proximity to the workplaces leads to reduction in stress of the workers. However, securing space for such facilities is not easy. In other words, there is room for improvement with respect to technology for reducing stress of workers at workplaces.

It would be helpful to improve technology for reducing stress of workers at workplaces.

An information processing apparatus according to the present disclosure is an information processing apparatus configured to manage a vehicle with a relaxation facility, the information processing apparatus including a controller configured to:

acquire stress information regarding a worker working at a workplace; and command the vehicle to move to the workplace based on the stress information.

A program according to the present disclosure is configured to cause an information processing apparatus to execute operations, the information processing apparatus being configured to manage a vehicle with a relaxation facility, the operations including:

acquiring stress information regarding a worker working at a workplace; and commanding the vehicle to move to the workplace based on the stress information.

An information processing method according to the present disclosure is an information processing method performed by an information processing apparatus configured to manage a vehicle with a relaxation facility, the information processing method including:

acquiring stress information regarding a worker working at a workplace; and commanding the vehicle to be dispatched to the workplace based on the stress information.

According to the present disclosure, technology for reducing stress of workers at workplaces can be improved.

DETAILED DESCRIPTION

An embodiment of the present disclosure will be described below with reference to the drawings.

Outline of Embodiment

Figure 1:
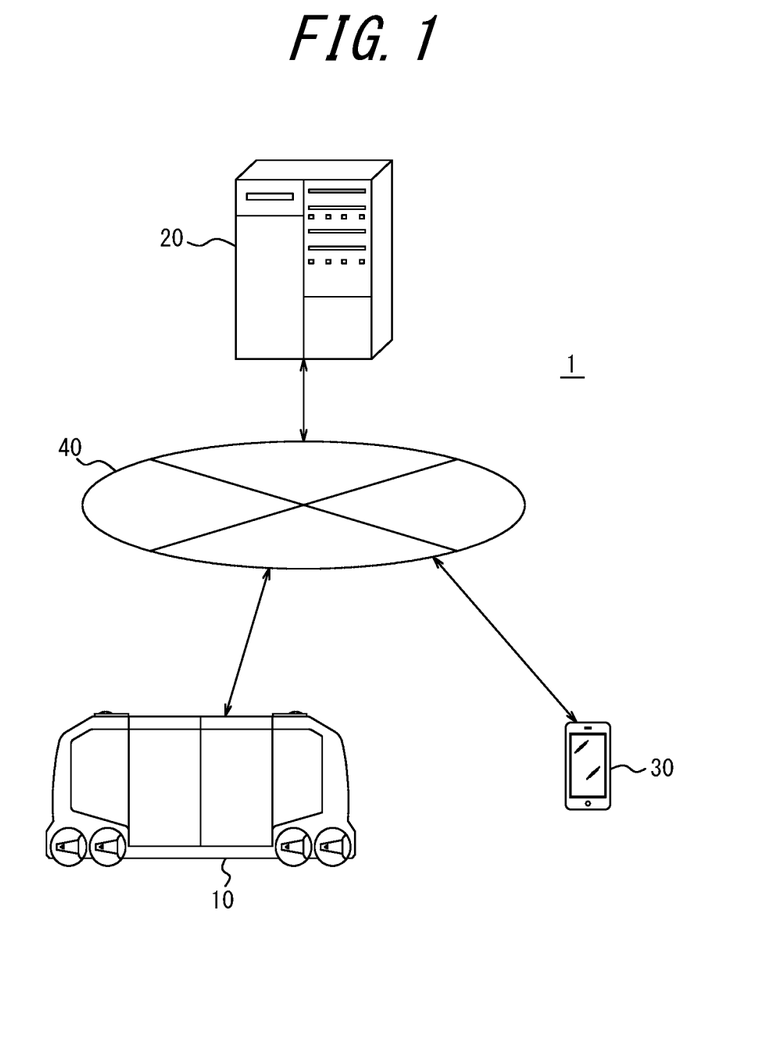
FIG. 1 is a diagram illustrating a configuration of a system according to an embodiment of the present disclosure.

An outline of a system 1 according to the embodiment of the present disclosure will be described with reference to FIG. 1. The system 1 includes a vehicle 10, an information processing apparatus 20, and a terminal apparatus 30. The vehicle 10, the information processing apparatus 20, and the terminal apparatus 30 are communicably connected to a network 40 including, for example, the Internet, a mobile communication network, and the like.

The vehicle 10 is an automobile, for example, but is not limited to this, and may be any appropriate vehicle. The vehicle 10 is, for example, a gasoline automobile, a battery electric vehicle (BEV), a hybrid electric vehicle (HEV), a plug-in hybrid electric vehicle (PHEV), a fuel cell electric vehicle (FCEV), or the like, but is not limited to these. The vehicle 10 includes a relaxation facility. The number of vehicles 10 provided in the system 1 may be freely determined. The vehicle 10 may be a manned vehicle or any autonomous vehicle that travels unmanned.

The information processing apparatus 20 is, for example, a dedicated computer configured to function as a server. The information processing apparatus 20 may be a general purpose personal computer (PC). The information processing apparatus 20 can communicate with the vehicle 10 and the terminal apparatus 30 via the network 40.

The terminal apparatus 30 is, for example, a general purpose electronic device such as a smartphone or a wearable terminal. The terminal apparatus 30 is an electronic device used, for example, by a worker who uses the relaxation facility of the vehicle 10. The terminal apparatus 30 is not limited to these, and may be an electronic device that is dedicated to the system 1.

First, an outline of the present embodiment will be described, and details thereof will be described later. The information processing apparatus 20 manages the vehicle 10 with the relaxation facility. The terminal apparatus 30 acquires stress information on a worker working at a workplace and transmits the stress information to the information processing apparatus 20. The information processing apparatus 20 acquires the stress information from the terminal apparatus 30. The information processing apparatus 20 then, based on the stress information, commands the vehicle 10 to move to the workplace.

As described above, according to the present embodiment, the information processing apparatus 20 acquires stress information on a worker and, based on the stress information, commands the vehicle 10 with the relaxation facility to move to a workplace of the worker. Thus, based on the stress information, the worker with a high probability of needing the relaxation facility can be encouraged to use the relaxation facility. For example, the worker can use the relaxation facility even in the workplace that has no relaxation facility. Therefore, technology for reducing stress of workers at workplaces can be improved in that, as long as the vehicle 10 can be dispatched to a workplace, workers at the workplace can be encouraged to use the relaxation facility.

Next, configurations of the system 1 will be described in detail.

(Configuration of Vehicle)

Figure 2:
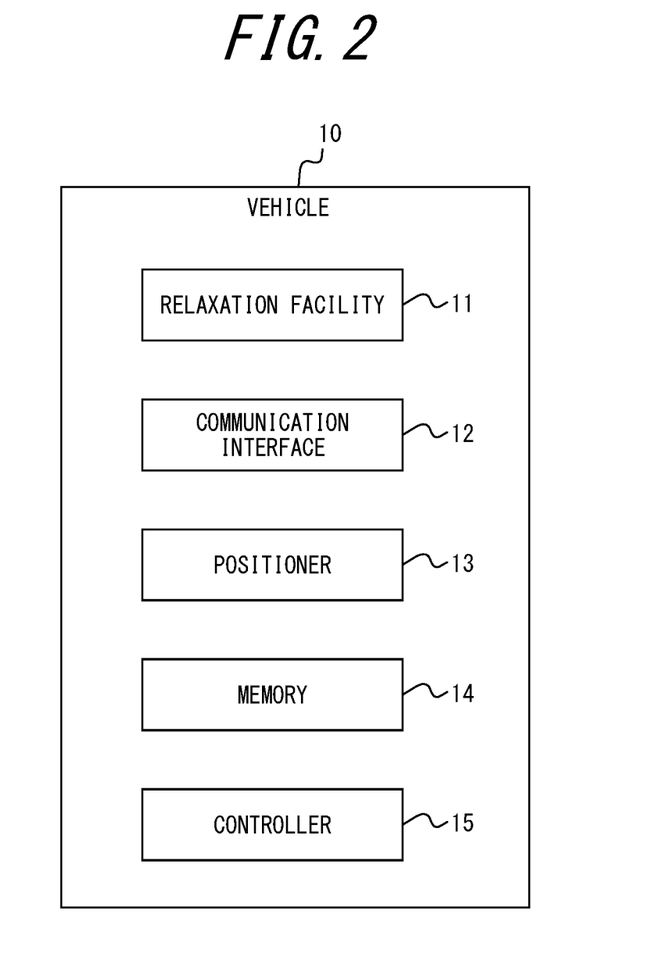
FIG. 2 is a block diagram illustrating a configuration of a vehicle according to the embodiment of the present disclosure.

As illustrated in FIG. 2, the vehicle 10 includes a relaxation facility 11, a communication interface 12, a positioner 13, a memory 14, and a controller 15.

The relaxation facility 11 include any stress-relieving facility provided in the vehicle 10. For example, the relaxation facility 11 includes a massage machine and/or an air purifier. The vehicle 10 may include a soundproof facility and/or a lavatory facility. The vehicle 10 may also include a shower, a bathroom facility, or the like. A massage provider, a massage practitioner, or the like may be on board the vehicle 10.

The communication interface 12 includes at least one communication interface for connecting to the network 40. The communication interface is compliant with mobile communication standards such as the 4th generation (4G) standard or the 5th generation (5G) standard, for example, but these examples are not limiting. In the present embodiment, the vehicle 10 communicates with the information processing apparatus 20 and the terminal apparatus 30 via the communication interface 12 and the network 40.

The positioner 13 includes one or more apparatuses configured to acquire positional information on the vehicle 10. Specifically, the positioner 13 includes a receiver corresponding to the Global Positioning System (GPS), for example, but is not limited to this, and may include a receiver corresponding to any satellite positioning system. The positioner 13 may acquire the positional information on the vehicle 10 continually, periodically, or non-periodically.

The memory 14 includes one or more memories. The memories are semiconductor memories, magnetic memories, optical memories, or the like, for example, but are not limited to these. The memories included in the memory 14 may each function as, for example, a main memory, an auxiliary memory, or a cache memory. The memory 14 stores any information used for operations of the vehicle 10. For example, the memory 14 may store a system program, an application program, embedded software, and the like. The information stored in the memory 14 may be updated with, for example, information acquired from the network 40 via the communication interface 12.

The controller 15 includes at least one processor, at least one programmable circuit, at least one dedicated circuit, or a combination of these. The processor is a general purpose processor such as a central processing unit (CPU) or a graphics processing unit (GPU), or a dedicated processor that is dedicated to specific processing, for example, but is not limited to these. The programmable circuit is a field-programmable gate array (FPGA), for example, but is not limited to this. The dedicated circuit is an application specific integrated circuit (ASIC), for example, but is not limited to this. The controller 15 controls the operations of the entire vehicle 10.

(Configuration of Information Processing Apparatus)

Figure 3:
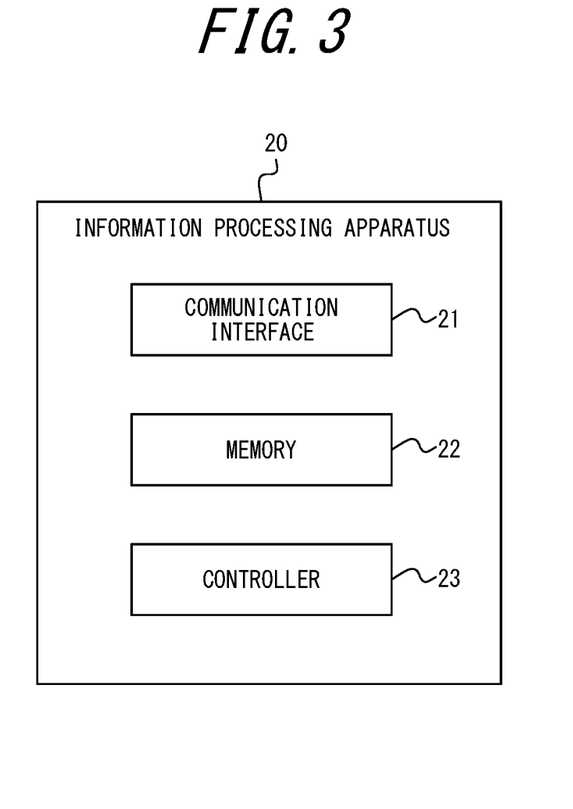
FIG. 3 is a block diagram illustrating a configuration of an information processing apparatus according to the embodiment of the present disclosure.

As illustrated in FIG. 3, the information processing apparatus 20 includes a communication interface 21, a memory 22, and a controller 23.

The communication interface 21 includes at least one communication interface for connecting to the network 40. The communication interface may be compliant with, for example, mobile communication standards, wired local area network (LAN) standards, or wireless LAN standards, but these examples are not limiting. The communication interface may be compliant with any appropriate communication standards. In the present embodiment, the information processing apparatus 20 communicates with the vehicle 10 and the terminal apparatus 30 via the communication interface 21 and the network 40. The information processing apparatus 20 may communicate via the communication interface 21 and the network 40 with vehicles other than the vehicle 10 according to the present embodiment, such as automobiles that do not have power supply capabilities, for example.

The memory 22 includes one or more memories. The memories included in the memory 22 may each function as, for example, a main memory, an auxiliary memory, or a cache memory. The memory 22 stores any information used for operations of the information processing apparatus 20. For example, the memory 22 may store a system program, an application program, a database, map information, and the like. The information stored in the memory 22 may be updated with, for example, information acquired from the network 40 via the communication interface 21.

The controller 23 includes at least one processor, at least one programmable circuit, at least one dedicated circuit, or a combination of these. The controller 23 controls the operations of the entire information processing apparatus 20.

(Configuration of Terminal Apparatus)

Figure 4:
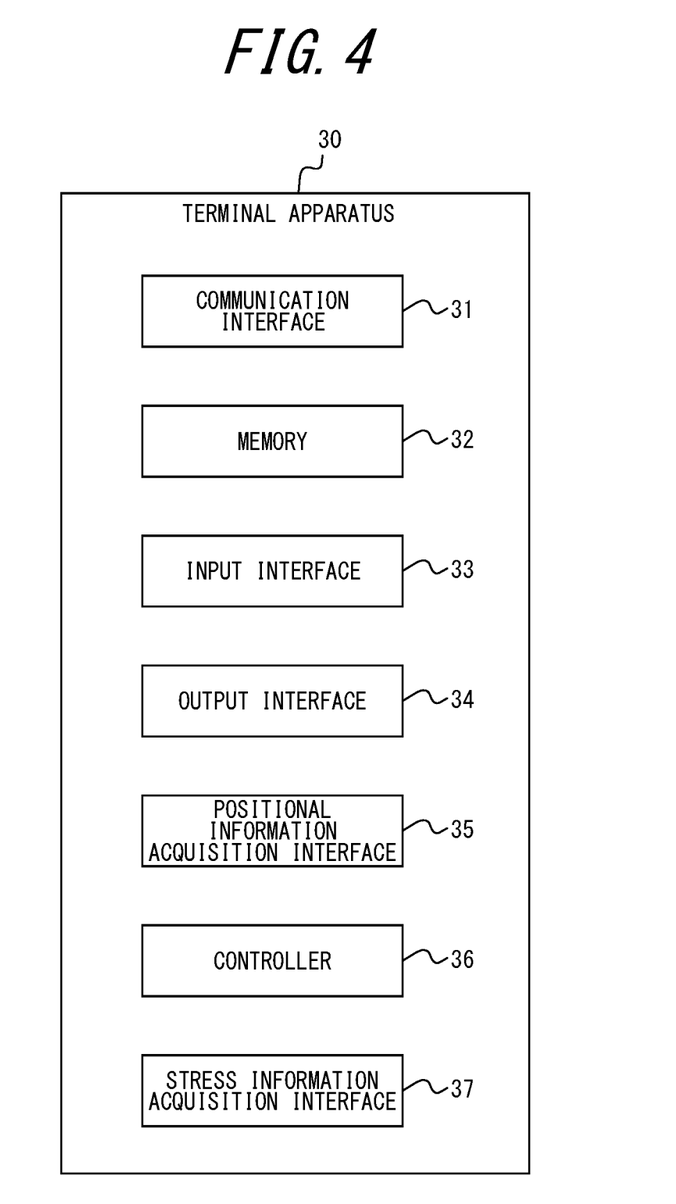
FIG. 4 is a block diagram illustrating a configuration of a terminal apparatus according to the embodiment of the present disclosure.

As illustrated in FIG. 4, the terminal apparatus 30 includes a communication interface 31, a memory 32, an input interface 33, an output interface 34, a positional information acquisition interface 35, a controller 36, and a stress information acquisition interface 37.

The communication interface 31 includes a communication module connected to the network 40. For example, the communication interface 21 may include a communication module compliant with mobile communication standards such as the 4th generation (4G) and the 5th generation (5G) standards. In an embodiment, the terminal apparatus 30 connects to the network 40 via the communication interface

31. The communication interface 31 transmits and receives various information via the network 40.

The memory 32 is, for example, a semi-conductor memory, a magnetic memory, an optical memory, or the like, but is not limited to these. The memory 32 may function as, for example, a main memory, an auxiliary memory, or a cache memory. The memory 32 stores any information used for operations of the terminal apparatus 30. For example, the memory 32 may store a system program, an application program, various types of information received by the communication interface 21, and the like. The information stored in the memory 32 may be updated with information received from the network 40 via the communication interface 31, for example.

The input interface 33 includes at least one input interface for detecting user input to acquire input information based on an operation by a user. The input interface 33 is, for example, a physical key, a capacitive key, a touch screen integrally provided with a display of the output interface 34, a microphone for receiving audio input, or the like, but is not limited to these.

The output interface 34 includes at least one output interface for outputting information to notify the user of the information. The output interface 34 is, for example, a display for outputting the information in the form of an image, a speaker for outputting the information in the form of audio, or the like, but is not limited to these.

The positional information acquisition interface 35 includes at least one device for acquiring positional information on the terminal apparatus 30. Specifically, the positional information acquisition interface 35 includes a receiver corresponding to the Global Positioning System (GPS), for example, but is not limited to this, and may include a receiver corresponding to any satellite positioning system. The positional information acquisition interface 35 may acquire the positional information on the terminal apparatus 30 continually, periodically, or non-periodically.

The controller 36 includes at least one processor, at least one programmable circuit, at least one dedicated circuit, or a combination of these. The controller 36 controls operations of the entire terminal apparatus 30.

The stress information acquisition interface 37 generates stress information on a worker. The stress information is any information that represents stress felt by the worker. The stress information may be qualitative or quantitative information. For example, the stress information acquisition interface 37 may be any sensor that detects vital information on the worker. Alternatively, the stress information acquisition interface 37 may acquire the stress information by performing image recognition processing on an image in which the worker's facial expression is captured and classifying the worker's facial expression. For example, the stress information acquisition interface 37 may be a dedicated processor that generates the stress information based on the vital information on the worker. The stress information acquisition interface 37 may also acquire vital information on the worker from an external device such as a wearable device and generate the stress information based on such vital information.

(Operations of System)

Figure 5:
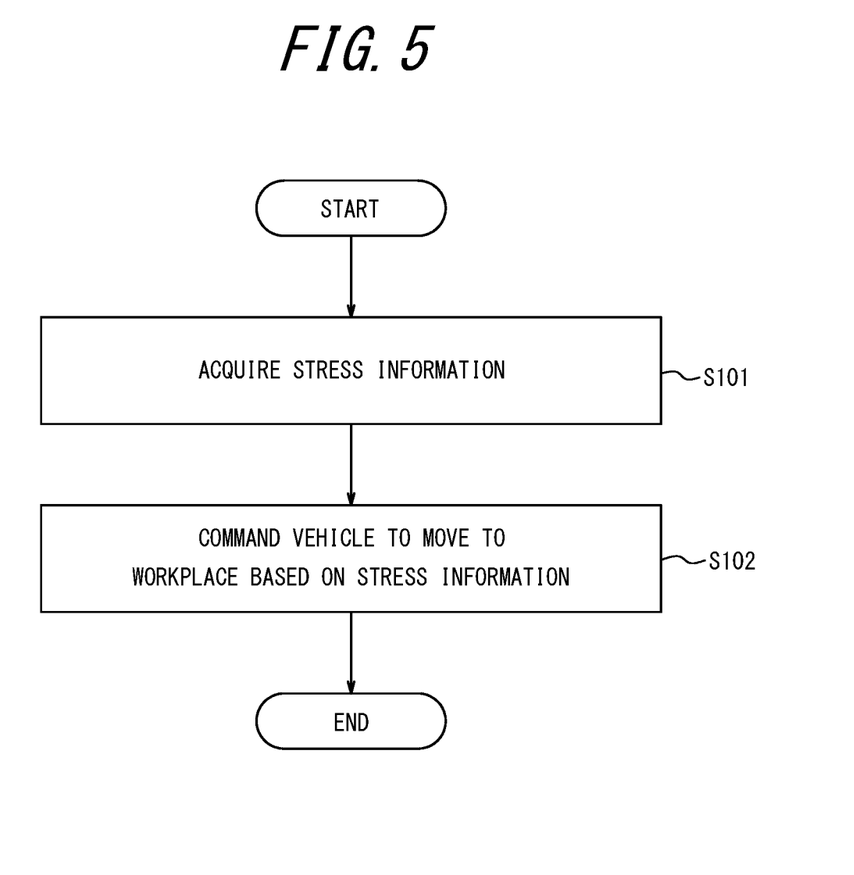
FIG. 5 is a flowchart illustrating operations of the system according to the embodiment of the present disclosure.

Operations of the system 1 according to the present embodiment will be described with reference to FIG. 5.

Step S101: The controller 23 of the information processing apparatus 20 acquires stress information regarding a worker working at a workplace.

Any method can be employed to acquire the stress information. For example, the controller 23 may acquire the stress information from the terminal apparatus 30 via the communication interface 21 and the network 40. Alternatively, the controller 23 may receive the stress information from an external server via the communication interface 21 and the network 40, or may calculate the stress information based on the worker's vital information received from the external server.

Step S102: Based on the stress information, the controller 23 commands the vehicle 10 to move to the workplace.

For example, the controller 23 detects an anomaly based on the stress information. Upon detecting such an anomaly, the controller 23 commands the vehicle 10 to move to the workplace at which the worker is present. In other words, upon detecting an anomaly based on the acquired stress information, the controller 23 dispatches the vehicle 10 with the relaxation facility 11 to the workplace of the worker.

As described above, the information processing apparatus 20 acquires stress information on a worker and, based on the stress information, commands the vehicle 10 with the relaxation facility to move to a workplace of the worker. Thus, based on the stress information, the worker with a high probability of needing the relaxation facility can be encouraged to use the relaxation facility.

(Variation 1 of Operations of System)

Figure 6:
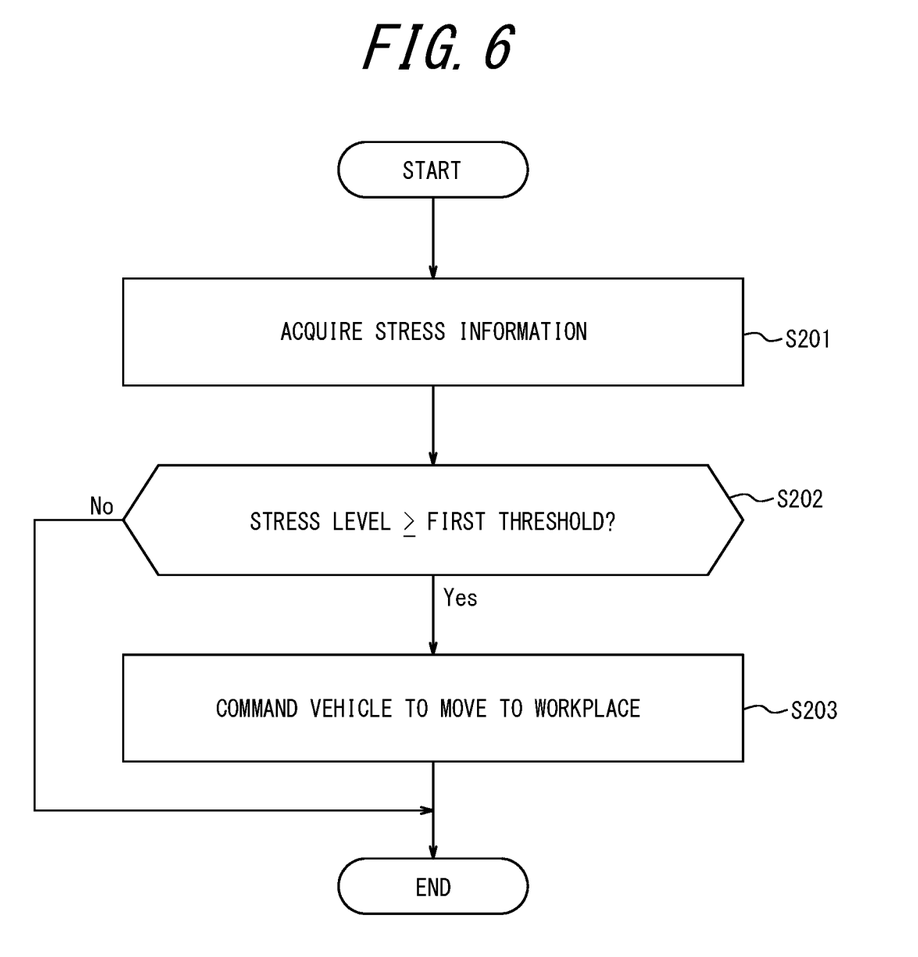
FIG. 6 is a flowchart illustrating a variation 1 of the operations of the system according to the embodiment of the present disclosure.

A variation 1 of the operations of the system 1 according to the present embodiment will be described with reference to FIG. 6.

Step S201: The controller 23 of the information processing apparatus 20 acquires stress information regarding a worker working at a workplace.

Such stress information includes a stress level of the worker. The stress level is quantitative information expressed, for example, as a numerical value on a scale of 100. The higher the value of the stress level, the higher the stress felt by the worker.

Step S202: The controller 23 determines whether the stress level is greater than or equal to a first threshold. The first threshold is determined based on a probability that workers need relaxation facilities. When the stress level is greater than or equal to the first threshold, the process proceeds to step S203. When the stress level is less than the first threshold, the process ends.

Step S203: When the stress level is greater than or equal to the first threshold, the controller 23 commands the vehicle 10 to move to the workplace.

As described above, the information processing apparatus 20 acquires stress information on a worker, and commands the vehicle 10 with the relaxation facility 11 to move to the worker's workplace when a stress level is greater than or equal to a first threshold. This allows the worker whose stress level is greater than or equal to the first threshold to be encouraged to use the relaxation facility 11.

(Variation 2 of Operations of System)

Figure 7:
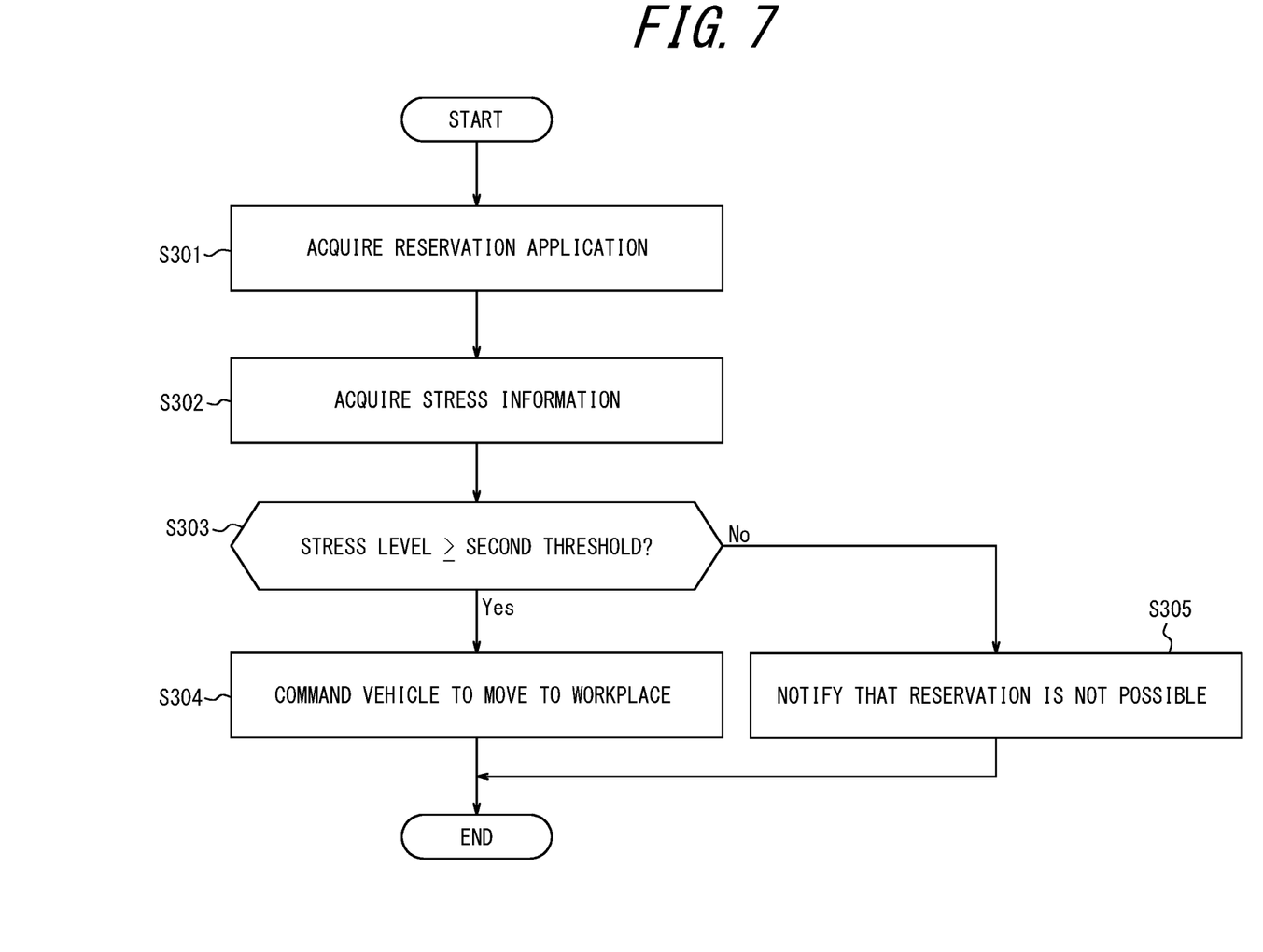
FIG. 7 is a flowchart illustrating a variation 2 of the operations of the system according to the embodiment of the present disclosure.

A variation 2 of the operations of the system 1 according to the present embodiment will be described with reference to FIG. 7.

Step S301: The controller 23 of the information processing apparatus 20 acquires a reservation application for the relaxation facility 11 from a worker working at a workplace.

Any method can be employed to acquire the reservation application. For example, the controller 23 may acquire the reservation application from the terminal apparatus 30 via the communication interface 21 and the network 40. Alternatively, the controller 23 may receive the reservation application from an external server via the communication interface 21 and the network 40.

Step S302: The controller 23 acquires stress information regarding a worker working at a workplace. Such stress information includes a stress level.

Step S303: The controller 23 determines whether the stress level is greater than or equal to a second threshold. The second threshold is determined based on a probability that workers need relaxation facilities. The second threshold may be the same as or different from the first threshold described above. When the stress level is greater than or equal to the second threshold, the process proceeds to step S304. When the stress level is less than the second threshold, the process proceeds to step S305.

Step S304: When the stress level is greater than or equal to the second threshold, the controller 23 commands the vehicle 10 to move to the workplace.

Step S305: When the stress level is less than the second threshold, the controller 23 notifies the worker that a reservation is not possible. Any appropriate method can be adopted to notify that a reservation is not possible. For example, the controller 23 may notify the terminal apparatus 30 that a reservation is not possible via the communication interface 21 and the network 40.

As described above, upon receiving a reservation application for the relaxation facility 11 from a worker, the information processing apparatus 20 acquires stress information on the worker, and commands the vehicle 10 with the relaxation facility 11 to move to the worker's workplace when a stress level is greater than or equal to a second threshold. This allows the worker whose stress level is greater than or equal to the second threshold to be encouraged to use the relaxation facility 11.

The second threshold may be a lower value than the first threshold, for example. This can encourage a worker whose stress level is lower than the first threshold and has a certain amount of leeway but is higher than the second threshold to use the relaxation facility 11. This allows workers whose stress levels have increased to some extent and who request to use the relaxation facility 11 to release stress early.

The reservation application may include a desired usage time frame for the relaxation facility 11. In this case, at step S303, the controller 23 commands the vehicle 10 to be dispatched to the workplace in the desired usage time period. In other words, the controller 23 commands the vehicle 10 to move to the workplace so that the worker can use the relaxation facility 11 in such a desired usage time period. This enables the worker to use the relaxation facility 11 in the desired usage time period.

The reservation application may include a desired usage time, and an upper limit of the desired usage time may be set according to the stress level. This enables the worker to use the relaxation facility 11 for a time length according to the stress level.

The reservation application may include the type of relaxation facility desired. In this case, at step S303, the controller 23 selects a vehicle 10 with the relaxation facility and commands the vehicle 10 to be dispatched to the workplace.

(Variation 3 of Operations of System)

Figure 8:
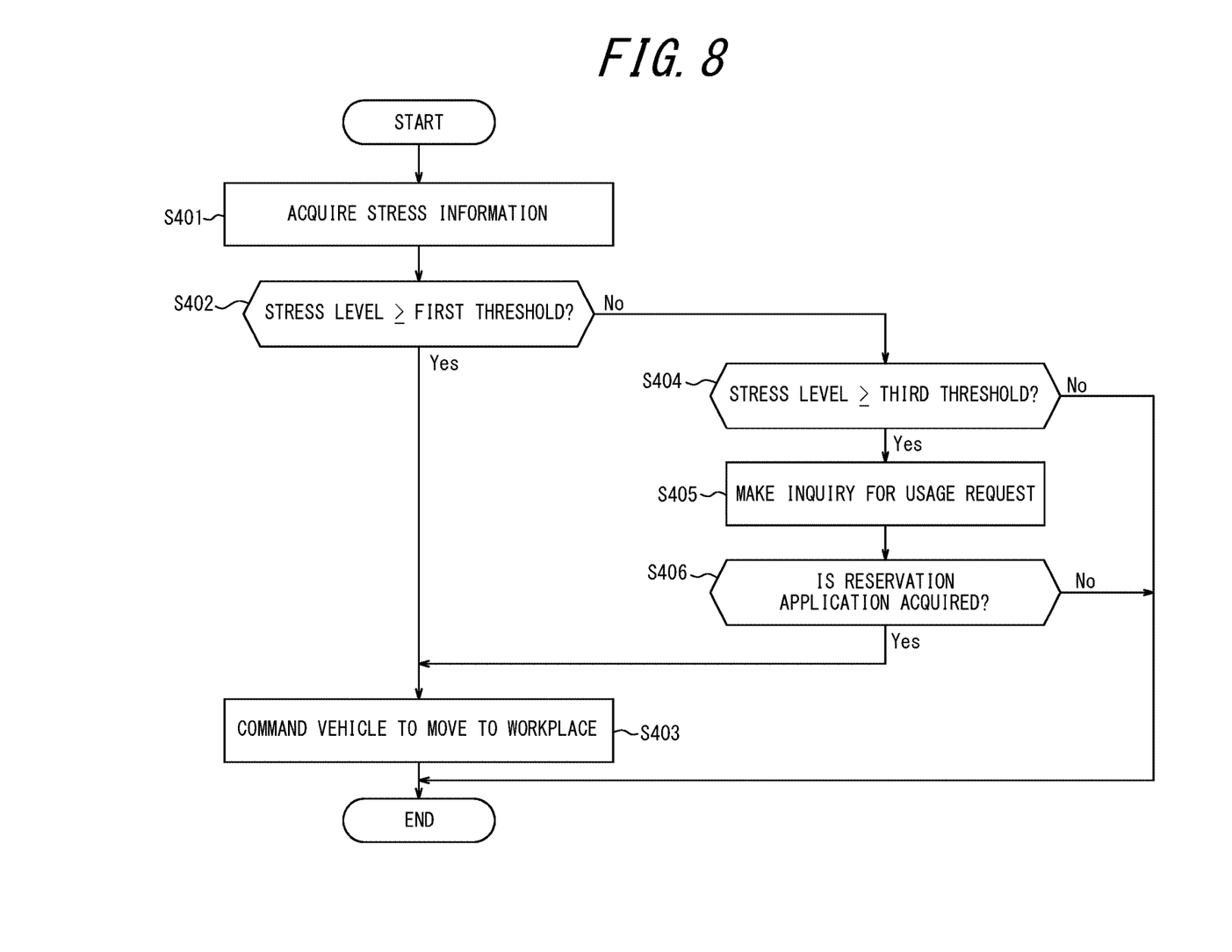
FIG. 8 is a flowchart illustrating a variation 3 of the operations of the system according to the embodiment of the present disclosure.

A variation 3 of the operations of the system 1 according to the present embodiment will be described with reference to FIG. 8.

Step S401: The controller 23 of the information processing apparatus 20 acquires stress information regarding a worker working at a workplace. Such stress information includes a stress level.

Step S402: The controller 23 determines whether the stress level is greater than or equal to a first threshold. When the stress level is greater than or equal to the first threshold, the process proceeds to step S403. When the stress level is less than the first threshold, the process proceeds to step S404.

Step S403: When the stress level is greater than or equal to the first threshold, the controller 23 commands the vehicle 10 to move to the workplace.

Step S404: When the stress level is less than the first threshold, the controller 23 determines whether the stress level is greater than or equal to a third threshold. The third threshold is determined based on a probability that workers need relaxation facilities. The third threshold is a lower value than the first threshold. When the stress level is greater than or equal to the third threshold, the process proceeds to step S405. When the stress level is less than the third threshold, the process ends.

Step S405: When the stress level is greater than or equal to the third threshold, the controller 23 makes an inquiry for a reservation application to the worker working at the workplace. Any method can be employed to make the inquiry for the reservation application. For example, the controller 23 may make the inquiry for the reservation application by sending a push notification regarding the reservation application to the terminal apparatus 30 via the communication interface 21 and the network 40.

Step S406: The controller 23 determines whether the reservation application is acquired. When it is determined that the reservation application is acquired, the process proceeds to step S403. When it is not determined that the reservation application is acquired, the process ends.

As described above, the information processing apparatus 20 acquires stress information on a worker, and commands the vehicle 10 with the relaxation facility 11 to move to the worker's workplace when a stress level is greater than or equal to a first threshold. This allows the worker whose stress level is greater than or equal to the first threshold to be encouraged to use the relaxation facility 11. In addition, since an inquiry for a reservation application is made to a worker whose stress level is less than the first threshold and greater than or equal to the third threshold, the use of the relaxation facility 11 can be encouraged for the worker whose stress level is less than the first threshold and has a certain degree of leeway, but is greater than or equal to the third threshold. This allows workers whose stress levels have increased to some extent and who request to use the relaxation facility 11 to release stress early.

As described above, according to the present embodiment, the information processing apparatus 20 acquires stress information on a worker and, based on the stress information, commands the vehicle 10 with the relaxation facility to move to a workplace of the worker. Thus, based on the stress information, the worker with a high probability of needing the relaxation facility 11 can be encouraged to use the relaxation facility 11. For example, the worker can use the relaxation facility 11 of the vehicle 10 even in the workplace that has no relaxation facility. Therefore, technology for reducing stress of workers at workplaces can be improved in that, as long as the vehicle 10 can be dispatched to a workplace, workers at the workplace can be encouraged to use the relaxation facility 11.

While the present disclosure has been described with reference to the drawings and examples, it should be noted that various modifications and revisions may be implemented by those skilled in the art based on the present disclosure. Accordingly, such modifications and revisions are included within the scope of the present disclosure. For example, functions or the like included in each component, each step, or the like can be rearranged without logical inconsistency, and a plurality of components, steps, or the like can be combined into one or divided.

For example, an embodiment in which the configuration and operations of the information processing apparatus 20 in the above embodiment are distributed to multiple computers capable of communicating with each other can be implemented. For example, an embodiment in which some or all of the components of the information processing apparatus 20 are provided in the vehicle 10 can also be implemented. For example, a navigation apparatus mounted in the vehicle 10 may be equipped with some or all of the components of the information processing apparatus 20.

For example, an embodiment in which a general purpose computer functions as the information processing apparatus 20 according to the above embodiment can also be implemented. Specifically, a program in which processes for realizing the functions of the information processing apparatus 20 according to the above embodiment are written may be stored in a memory of a general purpose computer, and the program may be read and executed by a processor. Accordingly, the present disclosure can also be implemented as a program executable by a processor, or a non-transitory computer readable medium storing the program.

For example, a configuration that causes a general purpose electronic device such as a smartphone, a computer, or the like to function as the information processing apparatus 20 according to the embodiment described above is possible. Specifically, a program in which processes for realizing the functions of the information processing apparatus 20 or the like according to the embodiment are written may be stored in a memory of the electronic device, and the program may be read and executed by a processor of the electronic device. Accordingly, in an embodiment, the present disclosure can also be implemented as a program executable by a processor.

Examples of some embodiments of the present disclosure are described below. However, it should be noted that the embodiments of the present disclosure are not limited to these examples.

[Appendix 1] An information processing apparatus configured to manage a vehicle with a relaxation facility, the information processing apparatus comprising a controller configured to:
acquire stress information regarding a worker working at a workplace; and
command the vehicle to move to the workplace based on the stress information.

[Appendix 2] The information processing apparatus according to appendix 1, wherein
the stress information includes a stress level of the worker, and
when the stress level is greater than or equal to a first threshold, the controller is configured to command the vehicle to move to the workplace.

[Appendix 3] The information processing apparatus according to appendix 1 or 2, wherein the vehicle includes a soundproof facility and/or a lavatory facility.

[Appendix 4] The information processing apparatus according to any one of appendices 1 to 3, wherein the relaxation facility includes a massage machine and/or an air purifier.

[Appendix 5] The information processing apparatus according to any one of appendices 1 to 4, wherein
the stress information includes a stress level of the worker, and
the controller is further configured to:
acquire a reservation application regarding the worker; and
when the stress level is greater than or equal to a second threshold, command the vehicle to move to the workplace based on the reservation application.

[Appendix 6] The information processing apparatus according to appendix 5, wherein
the reservation application includes a desired usage time period for the relaxation facility, and
the controller is configured to command the vehicle to be dispatched to the workplace in the desired usage time period.

[Appendix 7] The information processing apparatus according to any one of appendices 1 to 4, wherein the controller is configured to:
inquire a reservation application by the worker for the relaxation facility when the stress level is less than a first threshold and greater than or equal to a third threshold; and
command the vehicle to move to the workplace when the reservation application is acquired.

[Appendix 8] A program configured to cause an information processing apparatus to execute operations, the information processing apparatus being configured to manage a vehicle with a relaxation facility, the operations comprising:
acquiring stress information regarding a worker working at a workplace; and
commanding the vehicle to move to the workplace based on the stress information.

[Appendix 9] The program according to appendix 8, wherein
the stress information includes a stress level of the worker, and
when the stress level is greater than or equal to a first threshold, the operations comprise commanding the vehicle to move to the workplace.

[Appendix 10] The program according to appendix 9, wherein the vehicle includes a soundproof facility and/or a lavatory facility.

[Appendix 11] The program according to any one of appendices 8 to 10, wherein the relaxation facility includes a massage machine and/or an air purifier.

[Appendix 12] The program according to any one of appendices 8 to 11, wherein
the stress information includes a stress level of the worker, and
the operations comprise:
acquiring a reservation application regarding the worker; and
when the stress level is greater than or equal to a second threshold, commanding the vehicle to move to the workplace based on the reservation application.

[Appendix 13] The program according to appendix 12, wherein
the reservation application includes a desired usage time period for the relaxation facility, and
the operations comprise commanding the vehicle to move to the workplace in the desired usage time period.

[Appendix 14] The program according to any one of appendices 8 to 11, wherein the operations comprise:

inquiring a reservation application by the worker for the relaxation facility when the stress level is less than a first threshold and greater than or equal to a third threshold; and commanding the vehicle to move to the workplace when the reservation application is acquired.

[Appendix 15] An information processing method performed by an information processing apparatus configured to manage a vehicle with a relaxation facility, the information processing method comprising:

acquiring stress information regarding a worker working at a workplace; and commanding the vehicle to move to the workplace based on the stress information.

[Appendix 16] The information processing method according to appendix 15, wherein the stress information includes a stress level of the worker, and when the stress level is greater than or equal to a first threshold, the information processing method comprises commanding the vehicle to move to the workplace.

[Appendix 17] The information processing method according to appendix 15 or 16, wherein the vehicle includes a soundproof facility and/or a lavatory facility.

[Appendix 18] The information processing method according to any one of appendices 15 to 17, wherein the relaxation facility includes a massage machine and/or an air purifier.

[Appendix 19] The information processing method according to any one of appendices 15 to 18, wherein the stress information includes a stress level of the worker, and the information processing method comprises:

acquiring a reservation application regarding the worker; and when the stress level is greater than or equal to a second threshold, commanding the vehicle to move to the workplace based on the reservation application.

[Appendix 20] The information processing method according to appendix 19, wherein the reservation application includes a desired usage time period for the relaxation facility, and the information processing method comprises commanding the vehicle to be dispatched to the workplace in the desired usage time period.

The invention claimed is:

1. An information processing apparatus configured to control a vehicle with a relaxation facility, the information processing apparatus comprising a controller configured to:

receive, from a terminal apparatus of a worker working at a workplace, stress information including a stress level of the worker;

in a case that the stress level is greater than or equal to a first threshold, control the vehicle to autonomously move to the workplace; and in a case that the stress level is less than the first threshold and greater than or equal to a second threshold that is lower than the first threshold, transmit information inquiring for a reservation application for the relaxation facility to the terminal apparatus of the worker, and control the vehicle to autonomously move to the workplace in response to receiving the reservation application for the relaxation facility from the terminal apparatus of the worker.

2. The information processing apparatus according to claim 1, wherein the vehicle includes a soundproof facility and/or a lavatory facility.

3. The information processing apparatus according to claim 1, wherein the relaxation facility includes a massage machine and/or an air purifier.

4. The information processing apparatus according to claim 1, wherein the received reservation application includes a desired usage time period for the relaxation facility, and the controller is configured to control the vehicle to autonomously move to the workplace in the desired usage time period.

5. A non-transitory computer readable medium storing a program configured to cause an information processing apparatus to execute operations, the information processing apparatus being configured to control a vehicle with a relaxation facility, the operations comprising:

receiving, from a terminal apparatus of a worker working at a workplace, stress information including a stress level of the worker;

in a case that the stress level is greater than or equal to a first threshold, controlling the vehicle to autonomously move to the workplace; and in a case that the stress level is less than the first threshold and greater than or equal to a second threshold that is lower than the first threshold, transmitting information inquiring for a reservation application for the relaxation facility to the terminal apparatus of the worker, and controlling the vehicle to autonomously move to the workplace in response to receiving the reservation application for the relaxation facility from the terminal apparatus of the worker.

6. The non-transitory computer readable medium according to claim 5, wherein the vehicle includes a soundproof facility and/or a lavatory facility.

7. The non-transitory computer readable medium according to claim 5, wherein the relaxation facility includes a massage machine and/or an air purifier.

8. The non-transitory computer readable medium according to claim 5, wherein the received reservation application includes a desired usage time period for the relaxation facility, and the operations comprise controlling the vehicle to autonomously move to the workplace in the desired usage time period.

9. An information processing method performed by an information processing apparatus configured to control a vehicle with a relaxation facility, the information processing method comprising:

receiving, from a terminal apparatus of a worker working at a workplace, stress information including a stress level of the worker;

in a case that the stress level is greater than or equal to a first threshold, controlling the vehicle to autonomously move to the workplace; and in a case that the stress level is less than the first threshold and greater than or equal to a second threshold that is lower than the first threshold, transmitting information inquiring for a reservation application for the relaxation facility to the terminal apparatus of the worker, and controlling the vehicle to autonomously move to the workplace in response to receiving the reservation application for the relaxation facility from the terminal apparatus of the worker.

10. The information processing method according to claim 9, wherein the vehicle includes a soundproof facility and/or a lavatory facility.

11. The information processing method according to claim 9, wherein the relaxation facility includes a massage machine and/or an air purifier.

12. The information processing method according to claim 9, wherein
   the received reservation application includes a desired usage time period for the relaxation facility, and
   the information processing method comprises controlling the vehicle to autonomously move to the workplace in the desired usage time period.

13. The information processing apparatus according to claim 1, wherein the stress information is acquired by the terminal apparatus of the worker performing image recognition processing on an image in which facial expression of the worker is captured and classifying the facial expression of the worker.

* * * * *